US 9,560,956 B2

(12) United States Patent
Krupnik

(10) Patent No.: US 9,560,956 B2
(45) Date of Patent: Feb. 7, 2017

(54) DEVICE, SYSTEM AND METHOD OF DISPLAYING IN-VIVO IMAGES AT VARIABLE RATE

(71) Applicant: GIVEN IMAGING LTD., Yoqneam (IL)

(72) Inventor: Hagai Krupnik, Nofit (IL)

(73) Assignee: GIVEN IMAGING LTD., Yoqneam (IL)

( * ) Notice: Subject to any disclaimer, the term of this patent is extended or adjusted under 35 U.S.C. 154(b) by 0 days.

(21) Appl. No.: 14/035,653

(22) Filed: Sep. 24, 2013

(65) Prior Publication Data

US 2014/0022367 A1 Jan. 23, 2014

Related U.S. Application Data

(63) Continuation of application No. 11/508,940, filed on Aug. 24, 2006, now abandoned.

(51) Int. Cl.
*A61B 1/04* (2006.01)
*A61B 1/00* (2006.01)
*A61B 5/07* (2006.01)

(52) U.S. Cl.
CPC ............ *A61B 1/04* (2013.01); *A61B 1/0005* (2013.01); *A61B 1/00009* (2013.01); *A61B 1/041* (2013.01); *A61B 5/073* (2013.01)

(58) Field of Classification Search
CPC ............... H04N 5/23232; H04N 5/783; H04N 21/234381; H04N 21/440281; H04N 2201/3335
See application file for complete search history.

(56) References Cited

U.S. PATENT DOCUMENTS

| | | | |
|---|---|---|---|
| 4,278,077 A | 7/1981 | Mizumoto | |
| 5,604,531 A | 2/1997 | Iddan et al. | |
| 5,993,378 A | 11/1999 | Lemelson | |
| 6,172,712 B1 | 1/2001 | Beard | |
| 6,240,312 B1 | 5/2001 | Alfano et al. | |
| 6,709,387 B1 * | 3/2004 | Glukhovsky et al. | 600/109 |
| 6,760,536 B1 * | 7/2004 | Amir et al. | 386/344 |
| 7,009,634 B2 | 3/2006 | Iddan et al. | |
| 7,022,067 B2 | 4/2006 | Glukhovsky et al. | |
| 7,505,062 B2 * | 3/2009 | Davidson et al. | 348/77 |
| 7,813,590 B2 | 10/2010 | Horn et al. | |

(Continued)

FOREIGN PATENT DOCUMENTS

| | | |
|---|---|---|
| DE | 344 0177 | 5/1986 |
| JP | 57-45833 | 3/1982 |

(Continued)

OTHER PUBLICATIONS

Office Action Issued for U.S. Appl. No. 11/508,940, mailed Apr. 14, 2011.

(Continued)

*Primary Examiner* — Christopher Findley
(74) *Attorney, Agent, or Firm* — Pearl Cohen Zedek Latzer Baratz LLP

(57) ABSTRACT

Devices, systems and methods for displaying in-vivo images at variable rate. For example, a system includes a processor to gradually increase a frame display rate of an in-vivo image stream based on a similarity among two or more in-vivo frames of the in-vivo image stream.

20 Claims, 3 Drawing Sheets

(56) References Cited

U.S. PATENT DOCUMENTS

| | | | |
|---|---|---|---|
| 7,914,442 B1 | 3/2011 | Gazdzinski | |
| 8,249,425 B2* | 8/2012 | Ogikubo | .................. 386/278 |
| 2002/0080881 A1 | 6/2002 | Honda et al. | |
| 2002/0103417 A1 | 8/2002 | Gazdzinski | |
| 2002/0109774 A1 | 8/2002 | Meron et al. | |
| 2002/0111544 A1 | 8/2002 | Iddan | |
| 2003/0184598 A1 | 10/2003 | Graham | |
| 2006/0285732 A1 | 12/2006 | Horn et al. | |

FOREIGN PATENT DOCUMENTS

| | | |
|---|---|---|
| JP | 4-109927 | 4/1992 |
| JP | 1992-144533 | 5/1992 |

OTHER PUBLICATIONS

Final Office Action Issued for U.S. Appl. No. 11/508,940, mailed Aug. 2, 2011.
Office Action Issued for U.S. Appl. No. 11/508,940, mailed Oct. 4, 2012.
Final Office Action Issued for U.S. Appl. No. 11/508,940, mailed May 24, 2013.

\* cited by examiner

DEVICE, SYSTEM AND METHOD OF DISPLAYING IN-VIVO IMAGES AT VARIABLE RATE

CROSS-REFERENCE TO RELATED APPLICATIONS

This application is a continuation of U.S. patent application Ser. No. 11/508,940, filed Aug. 24, 2006, which is hereby incorporated by reference.

FIELD OF THE INVENTION

The present invention relates to the field of in-vivo sensing, for example, in-vivo imaging.

BACKGROUND OF THE INVENTION

Some in-vivo sensing systems may include an in-vivo imaging device able to acquire and transmit images of, for example, the GI tract while the in-vivo imaging device passes through the GI lumen.

Other devices, systems and methods for in-vivo sensing of passages or cavities within a body, and for sensing and gathering information (e.g., image information, pH information, temperature information, electrical impedance information, pressure information, etc.), are known in the art.

Some in-vivo imaging devices may acquire a large number of in-vivo images, for example, hundreds or thousands of in-vivo images, e.g., over a period of several hours. Accordingly, a relatively long time period may be required from a physician in order to view the acquired in-vivo images.

SUMMARY OF THE INVENTION

Some embodiments of the present invention may include, for example, devices, systems and methods for displaying in-vivo images at variable rate.

In some embodiments, for example, a system may include a processor to gradually increase a frame display rate of an in-vivo image stream based on a similarity among two or more in-vivo frames of the in-vivo image stream.

In some embodiments, for example, the processor may gradually increase the frame display rate until a pre-defined maximum frame display rate is reached.

In some embodiments, for example, the processor may non-gradually decrease the frame display rate upon detection of a difference between the two or more in-vivo frames.

In some embodiments, for example, the processor may reset the frame display rate from an accelerated frame display rate to a non-accelerated frame display rate upon detection of the difference.

In some embodiments, for example, the processor may reset the frame display rate from an accelerated frame display rate to a non-accelerated frame display rate in response to a command to begin displaying the in-vivo image stream from a selected point.

In some embodiments, for example, the processor may detect the similarity based on a comparative analysis of two or more of the in-vivo frames.

In some embodiments, for example, the processor may perform the comparative analysis during a time period in which at least a portion of the in-vivo image stream is displayed.

In some embodiments, for example, the in-vivo image stream includes a non-processed in-vivo image stream.

In some embodiments, for example, the system may further include a display unit to display the in-vivo image stream at the frame display rate.

In some embodiments, for example, the display unit may display an indication that the in-vivo image stream is displayed at an accelerated frame display rate.

In some embodiments, for example, the system may further include an in-vivo imaging device including an imager to acquire the plurality of in-vivo frames.

In some embodiments, for example, the in-vivo imaging device may be autonomous.

In some embodiments, for example, the in-vivo imaging device may include a swallowable capsule.

In some embodiments, for example, a method may include gradually increasing a frame display rate of an in-vivo image stream based on a similarity among two or more in-vivo frames of the in-vivo image stream.

In some embodiments, for example, the method may include gradually increasing the frame display rate until a pre-defined maximum frame display rate is reached.

In some embodiments, for example, the method may include non-gradually decreasing the frame display rate upon detection of a difference between the two or more in-vivo frames.

In some embodiments, for example, the method may include resetting the frame display rate from an accelerated frame display rate to a non-accelerated frame display rate upon detection of the difference.

In some embodiments, for example, the method may include resetting the frame display rate from an accelerated frame display rate to a non-accelerated frame display rate in response to a command to begin displaying the in-vivo image stream from a selected point.

In some embodiments, for example, the method may include detecting the similarity based on a comparative analysis of two or more of the in-vivo frames.

In some embodiments, for example, the method may include performing the comparative analysis during a time period in which at least a portion of the in-vivo image stream is displayed.

Embodiments of the invention may provide various other benefits and/or advantages.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1:
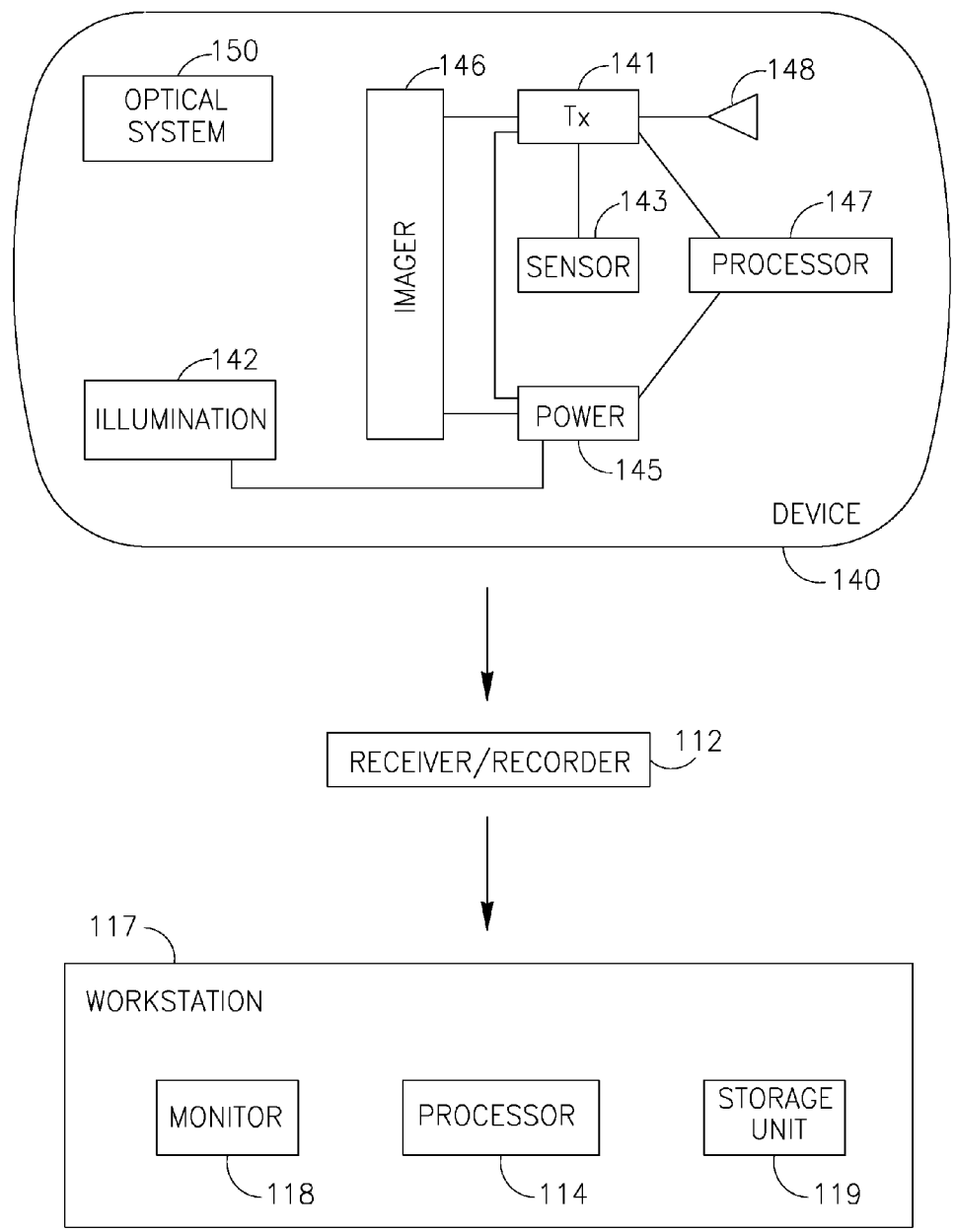
FIG. 1 is a schematic illustration of an in-vivo system according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate,

DETAILED DESCRIPTION OF THE INVENTION

In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Although a portion of the discussion may relate to in-vivo imaging devices, systems, and methods, the present invention is not limited in this regard, and some embodiments of the present invention may be used in conjunction with various other in-vivo sensing devices, systems, and methods. For example, some embodiments of the invention may be used, for example, in conjunction with in-vivo sensing of pH, in-vivo sensing of temperature, in-vivo sensing of pressure, in-vivo sensing of electrical impedance, in-vivo detection of a substance or a material, in-vivo detection of a medical condition or a pathology, in-vivo acquisition or analysis of data, and/or various other in-vivo sensing devices, systems, and methods.

Some embodiments of the present invention are directed to a typically one time use or partially single use detection and/or analysis device. Some embodiments are directed to a typically swallowable in-vivo device that may passively or actively progress through a body lumen, e.g., the gastro-intestinal (GI) tract, for example, pushed along by natural peristalsis. Some embodiments are directed to in-vivo sensing devices that may be passed through other body lumens, for example, through blood vessels, the reproductive tract, or the like. The in-vivo device may be, for example, a sensing device, an imaging device, a diagnostic device, a detection device, an analysis device, a therapeutic device, or a combination thereof. In some embodiments, the in-vivo device may include an image sensor or an imager. Other sensors may be included, for example, a pH sensor, a temperature sensor, a pressure sensor, sensors of other in-vivo parameters, sensors of various in-vivo substances or compounds, or the like.

Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. Pat. No. 7,009,634 to Iddan et al., entitled "Device for In-Vivo Imaging", and/or in U.S. patent application Ser. No. 10/046,541, entitled "System and Method for Wide Field Imaging of Body Lumens", filed on Jan. 16, 2002, published on Aug. 15, 2002 as United States Patent Application Publication Number 2002/0109774, and/or in U.S. patent application Ser. No. 10/046,540, entitled "System and Method for Determining In-vivo Body Lumen Conditions", filed on Jan. 16, 2002, published on Aug. 15, 2002 as United States Patent Application Publication Number 2002/0111544, and/or in U.S. Pat. No. 6,709,387 to Glukhovsky et al., entitled "System and Method for Controlling In Vivo Camera Capture and Display Rate", and/or in U.S. Pat. No. 7,022,067 to Glukhovsky et al., entitled "System and Method for Controlling In Vivo Camera Capture and Display Rate", all of which are hereby incorporated by reference in their entirety. Devices and systems as described herein may have other configurations and/or sets of components. For example, an external receiver/recorder unit, a processor and a monitor, e.g., in a workstation, such as those described in the above publications, may be suitable for use with some embodiments of the present invention. Devices and systems as described herein may have other configurations and/or other sets of components. For example, the present invention may be practiced using an endoscope, needle, stent, catheter, etc. Some in-vivo devices may be capsule shaped, or may have other shapes, for example, a peanut shape or tubular, spherical, conical, or other suitable shapes.

Some embodiments of the present invention may include, for example, a typically swallowable in-vivo device. In other embodiments, an in-vivo device need not be swallowable and/or autonomous, and may have other shapes or configurations. Some embodiments may be used in various body lumens, for example, the GI tract, blood vessels, the urinary tract, the reproductive tract, or the like. In some embodiments, the in-vivo device may optionally include a sensor, an imager, and/or other suitable components.

Embodiments of the in-vivo device are typically autonomous and are typically self-contained. For example, the in-vivo device may be or may include a capsule or other unit where all the components are substantially contained within a container, housing or shell, and where the in-vivo device does not require any wires or cables to, for example, receive power or transmit information. The in-vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units; and control information or other information may be received from an external source.

Devices, systems and methods in accordance with some embodiments of the invention may be used, for example, in conjunction with a device which may be inserted into a human body or swallowed by a person. However, embodiments of the invention are not limited in this regard, and may be used, for example, in conjunction with a device which may be inserted into, or swallowed by, a non-human body or an animal body.

FIG. 1 schematically illustrates an in-vivo system in accordance with some embodiments of the present invention. One or more components of the system may be used in conjunction with, or may be operatively associated with, the devices and/or components described herein or other in-vivo devices in accordance with embodiments of the invention.

In some embodiments, the system may include a device 140 having a sensor, e.g., an imager 146, one or more illumination sources 142, a power source 145, and a transmitter 141. In some embodiments, device 140 may be implemented using a swallowable capsule, but other sorts of devices or suitable implementations may be used. Outside a patient's body may be, for example, an external receiver/recorder 112 (including, or operatively associated with, for example, one or more antennas, or an antenna array), a storage unit 119, a processor 114, and a monitor 118. In some embodiments, for example, processor 114, storage unit 119 and/or monitor 118 may be implemented as a workstation 117, e.g., a computer or a computing platform.

Transmitter 141 may operate using radio waves; but in some embodiments, such as those where device 140 is or is included within an endoscope, transmitter 141 may transmit/ receive data via, for example, wire, optical fiber and/or other suitable methods. Other known wireless methods of transmission may be used. Transmitter 141 may include, for example, a transmitter module or sub-unit and a receiver module or sub-unit, or an integrated transceiver or transmitter-receiver.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit information. In some embodiments, device 140 may be autonomous and non-remote-controllable; in another embodiment, device 140 may be partially or entirely remote-controllable.

In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

In some embodiments, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 in device 140 may be operationally connected to transmitter 141. Transmitter 141 may transmit images to, for example, external transceiver or receiver/recorder 112 (e.g., through one or more antennas), which may send the data to processor 114 and/or to storage unit 119. Transmitter 141 may also include control capability, although control capability may be included in a separate component, e.g., processor 147. Transmitter 141 may include any suitable transmitter able to transmit image data, other sensed data, and/or other data (e.g., control data) to a receiving device. Transmitter 141 may also be capable of receiving signals/commands, for example from an external transceiver. For example, in some embodiments, transmitter 141 may include an ultra low power Radio Frequency (RF) high bandwidth transmitter, possibly provided in Chip Scale Package (CSP).

In some embodiment, transmitter 141 may transmit/receive via antenna 148. Transmitter 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transmitter 141 may include a receiver which may receive signals (e.g., from outside the patient's body), for example, through antenna 148 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

In some embodiments, power source 145 may be internal to device 140, and/or may not require coupling to an external power source, e.g., to receive power. Power source 145 may provide power to one or more components of device 140 continuously, substantially continuously, or in a non-discrete manner or timing, or in a periodic manner, an intermittent manner, or an otherwise non-continuous manner. In some embodiments, power source 145 may provide power to one or more components of device 140, for example, not necessarily upon-demand, or not necessarily upon a triggering event or an external activation or external excitement.

Optionally, in some embodiments, transmitter 141 may include a processing unit or processor or controller, for example, to process signals and/or data generated by imager 146. In another embodiment, the processing unit may be implemented using a separate component within device 140, e.g., controller or processor 147, or may be implemented as an integral part of imager 146, transmitter 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transmitter 141, and may be implemented, for example, using an ASIC.

In some embodiments, imager 146 may acquire in-vivo images continuously, substantially continuously, or in a non-discrete manner, for example, not necessarily upon-demand, or not necessarily upon a triggering event or an external activation or external excitement; or in a periodic manner, an intermittent manner, or an otherwise non-continuous manner.

In some embodiments, transmitter 141 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optional optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminated light, and/or performing other light processing operations.

In some embodiments, illumination source(s) 142 may illuminate continuously, or substantially continuously, for example, not necessarily upon-demand, or not necessarily upon a triggering event or an external activation or external excitement. In some embodiments, for example, illumination source(s) 142 may illuminate a pre-defined number of times per second (e.g., two or four times), substantially continuously, e.g., for a time period of two hours, four hours, eight hours, or the like; or in a periodic manner, an intermittent manner, or an otherwise non-continuous manner.

In some embodiments, the components of device 140 may be enclosed within a housing or shell, e.g., capsule-shaped, oval, or having other suitable shapes. The housing or shell may be substantially transparent or semi-transparent, and/or may include one or more portions, windows or domes which may be substantially transparent or semi-transparent. For example, one or more illumination source(s) 142 within device 140 may illuminate a body lumen through a transparent or semi-transparent portion, window or dome; and light reflected from the body lumen may enter the device 140, for example, through the same transparent or semi-transparent portion, window or dome, or, optionally, through another transparent or semi-transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to external receiver/recorder 112. Other constant and/or variable capture rates and/or transmission rates may be used.

Typically, the image data recorded and transmitted may include digital color image data; in alternate embodiments, other image formats (e.g., black and white image data) may be used. In some embodiments, each frame of image data may include 256 rows, each row may include 256 pixels, and each pixel may include data for color and brightness according to known methods. According to other embodiments a 320×320 pixel imager may be used. Pixel size may be between 5 to 6 micron. According to some embodiments pixels may be each fitted with a micro lens. For example, a Bayer color filter may be applied. Other suitable data formats may be used, and other suitable numbers or types of rows, columns, arrays, pixels, sub-pixels, boxes, super-pixels and/or colors may be used.

Optionally, device 140 may include one or more sensors 143, instead of or in addition to a sensor such as imager 146. Sensor 143 may, for example, sense, detect, determine and/or measure one or more values of properties or characteristics of the surrounding of device 140. For example, sensor 143 may include a pH sensor, a temperature sensor, an electrical conductivity sensor, a pressure sensor, or any other known suitable in-vivo sensor.

In some embodiments, device 140 may acquire a large number of in-vivo images, for example, hundreds or thousands of in-vivo images, e.g., over several hours. For example, an image stream or a video stream acquired by device 140 may include hundreds or thousands of in-vivo images or in-vivo frames. The in-vivo image stream may include multiple portions, which may be characterized in accordance with one or more characteristics.

For example, in some embodiments, a first portion of an in-vivo image stream may be relatively or substantially repetitive, static, non-changing, constant, slowly-changing, or the like ("a static portion"). For example, a first in-vivo image of the static portion of the image stream may be identical, substantially identical, similar or substantially similar to a second (e.g., consecutive) in-vivo image of the static portion of the in-vivo stream. In some embodiments, for example, a scenery, an imaged object, or an imaged field-of-view may be substantially unmodified or substantially unchanging over multiple (e.g., consecutive) in-vivo images of the static portion of the in-vivo stream. A static portion of the in-vivo image stream may correspond, for example, to a time period in which the in-vivo imaging device is substantially static or non-moving, is moving relatively slowly, is moving through a portion of a body lumen having unchanging properties, or the like.

In contrast, for example, a second portion of an in-vivo image stream may be relatively dynamic, changing, non-repetitive, non-static, or the like ("a dynamic portion"). For example, a first in-vivo image of the dynamic portion of the image stream may be different, or substantially different, from a second (e.g., consecutive) in-vivo image of the dynamic portion of the in-vivo stream. In one embodiment, for example, a scenery, an imaged object, or an imaged field-of-view may appear substantially modified or different over multiple (e.g., consecutive) in-vivo images of the static portion of the in-vivo stream. In another embodiment, for example, a first image of the dynamic portion of the image stream may include a first imaged object or area, whereas a second image of the dynamic portion of the image stream may include a second, different, imaged object or area. A dynamic portion of the in-vivo image stream may correspond, for example, to a time period in which the in-vivo imaging device is substantially dynamic and moving, is moving relatively fast, is moving through a portion of a body lumen having changing properties, or the like.

In accordance with some embodiments of the invention, a first (e.g., higher) frame display rate may be used to display in-vivo images of a first portion of the image stream (e.g., a static portion); whereas a second (e.g., smaller) frame display rate may be used to display in-vivo images of a second portion of the image stream (e.g., a dynamic portion). In some embodiments, for example, processor 114 and/or workstation 117 may identify one or more portions of the in-vivo image streams as static portions or as dynamic portions, and may associate such portions with one or more constant and/or changing (e.g., accelerated) frame display rate. In some embodiments, operations of identification, comparison, analysis and/or determination (e.g., determination to accelerate or decelerate the frame display rate) may optionally be performed by one or more other units, for example, by receiver/recorder 112, e.g., using a processor or controller or sub-unit of receiver/recorder 112, or by other suitable units or sub-units of the system of FIG. 1.

In one embodiment, the identification of static portions and/or dynamic portions of the in-vivo image stream may be performed substantially in real time or in display time, for example, while a portion of the in-vivo image stream is displayed; in another embodiment, the identification of static portions and/or dynamic portions of the in-vivo image stream may be performed during a pre-processing stage, e.g., prior to displaying the in-vivo images to a physician.

In one embodiment, for example, a pre-processing of the in-vivo image stream may not be performed and/or may not be required; for example, image analysis may begin at a starting point or a starting time selected by the user (e.g., for display), such that the in-vivo image corresponding to the selected starting point or starting time may be used as the first image of reference and the frame display rate at that image may be set to the "basic" frame display rate. This may be performed, for example, even if the user selects to start viewing the image stream from a point located within a generally static portion of the image stream. In some embodiments, a pre-processing stage (e.g., image comparison stage or image analysis stage) may be used, for example, to determine in advance (e.g., prior to actual presentation of the in-vivo image stream) a degree of similarity or a degree of difference among in-vivo images; whereas the frame display rate being used may be determined and/or modified substantially in real time or in display time, e.g., during a presentation of the in-vivo image stream, for example, taking into account an initial frame display rate used upon beginning or resuming of the presentation. Other suitable timing combinations may be used in conjunction with analysis operations, comparison operations, determination operations, modification of frame display rate, or the like.

In some embodiments, a physician may request to playback (e.g., to display) or to present the in-vivo image stream, for example, starting at a certain starting point or starting time. The starting point or starting time may be indicated or selected by the physician, for example, using a time bar, a counter, a clock mechanism, a progress bar, a timeline, an in-vivo location bar, an in-vivo location indicator, or the like. In one embodiment, the starting point or starting time may be the beginning of the acquired in-vivo image stream; in another embodiment, the starting point or starting time may correspond to a certain, non-initial frame of the in-vivo image stream. In some embodiments, the physician may utilize the workstation 117 to selectively pause, stop, play or replay portions of the in-vivo image stream.

In some embodiments, a first frame display rate ("basic frame display rate") may be utilized to display in-vivo images in response to a request (e.g., by the physician) to begin presentation of the in-vivo image stream or to begin presentation at a certain point or time of the in-vivo image stream. The basic frame display rate may be, for example, a constant or a substantially constant frame display rate, such that a constant number of frames is displayed per second or per minute. The basic frame display rate may be, for example, a relatively low frame display rate, e.g., approximately five frames per second. This may allow the physician, for example, to view the in-vivo image stream at a relatively slow or "normal" pace, at substantially any point in which the physician selects to begin (or restart) the viewing.

In some embodiments, it may be determined, for example, by processor 114 or by workstation 117, that in-vivo images are substantially repetitive, identical or substantially similar, or belong to a static portion of the in-vivo image stream. In response to such determination, workstation 117 may increase, e.g., gradually, the frame display rate ("accelerated frame display rate"), for example, until a pre-defined maximum threshold value of frame display rate is reached. The positive acceleration of the frame display rate may allow displaying, e.g., to the physician, the in-vivo images more rapidly or using an "accelerated" pace, for example, since the in-vivo images are substantially repetitive, identical, similar or non-changing. In some embodiments, for example, the "accelerated" frame display rate may be, for example, twice the "basic" frame display rate, three time the "basic" frame display rate, four times the "basic" frame display rate, five times the "basic" frame display rate, or the like. In some embodiments, the value of the maximum threshold of accelerated frame display rate may be, for example, approximately four or five times the "basic" frame display rate, approximately 20 or 25 frames per second, or other suitable values.

In some embodiments, a change in scenery may be detected, for example, by processor 114 or workstation 117, e.g., such that the in-vivo image stream is about to display an in-vivo image which is substantially different or significantly different from the previously-displayed in-vivo image. Upon detection of such change or difference among the acquired in-vivo images, processor 114 or workstation 117 may change (e.g., decrease or reset) the frame display rate, e.g., to the basic frame display rate. The negative acceleration, the deceleration, or the resetting of the frame display rate (e.g., resetting to the basic frame display rate) may allow workstation 117 to display in-vivo images at the "normal" or basic (e.g., slow) pace, for example, upon detection of the change in the in-vivo image stream.

Some embodiments, for example, may provide an improved and/or more efficient user experience to a user (e.g., a physician) who views an in-vivo image stream, e.g., a relatively long in-vivo image stream. For example, a constant frame display rate may cause the user to feel bored during static or repetitive portions of the in-vivo image stream, and/or to feel anxious or stressed during dynamic or changing portions of the in-vivo image stream. In some embodiments, for example, workstation 117 may substantially automatically accelerate (e.g., gradually) the frame display rate during a static portion of the in-vivo stream, e.g., up to a pre-defined maximum threshold frame display rate; and workstation 117 may decrease (e.g., immediately or non-gradually) the frame display rate upon detection of a difference or a change between in-vivo images in the stream. In some embodiments, workstation 117 may thus "alert" the user to a changing imaged scenery by decelerating the frame display rate, e.g., by immediately resetting the frame display rate to the "basic" (e.g., normal or slow) frame display rate. In some embodiments, workstation 117 may automatically or semi-automatically (e.g., based on user's input) adjust or modify the frame display rate being used, for example, in order to meet a need of the user (e.g., a physician) to detect certain information in the in-vivo image stream and/or to detect a possible pathologies which may be included in the in-vivo image stream or in a portion thereof. In some embodiments, workstation 117 may automatically or semi-automatically (e.g., based on user's input) anticipate a need of the user (e.g., a physician) to view a portion of the in-vivo stream at a certain frame display rate, e.g., to view a dynamic portion of the in-vivo image stream at a "basic" or decreased frame display rate, to view a static portion of the in-vivo image stream at an accelerated or increased frame display rate, or the like.

In some embodiments, the "basic" frame display rate may be pre-defined, or may be selectable or modifiable by a user (e.g., in substantially real time or in display time, while the in-vivo stream is displayed). For example, in one embodiment, workstation 117 may display a "slider" or other bar or modifier allowing the user to select or modify the "basic" frame display rate. For example, the user may set the "basic" frame display rate to a certain rate (e.g., two frames per second), and may later modify the "basic" frame display rate to another rate (e.g., three frames per second). In some embodiments, the value of the "basic" frame display rate may optionally be selected by a user (e.g., a physician), for example, based on a preference of the user, based on the frame display rate at which the user feels comfortable to view the in-vivo image stream, taking into account the expertise or the experience of the user in reviewing the in-vivo image stream, or the like. In some embodiments, the value of the "basic" frame display rate may be set, for example, by asking the user to select or indicate his level of expertise (e.g., a beginner level, an average level, an expert or advanced level), and assigning a higher value to the "basic" frame display rate for higher or increased expertise of the user. In some embodiments, optionally, the "basic" frame display rate may be determined or set based on an indication from the user of the period of time that he wishes to allocate to reviewing the in-vivo image stream; for example, a higher value may be set to the "basic" frame display rate if the user indicates that the user allocates a relatively short period of time to reviewing the in-vivo image stream, and vice versa. Other suitable methods may be used to select, set or determine the value of the "basic" frame display rate.

In some embodiments, the "accelerated" frame display rate may be pre-defined or preset (e.g., as a pre-defined number of frames per seconds), or may be dynamically calculated relative to the "basic" frame display rate, e.g., as a multiply (e.g., an integer multiply greater than one, or a non-integer multiply greater than one) of the "basic" frame display rate.

In some embodiments, one or more methods may be used to determine whether to accelerate (e.g., increase), to maintain, or to decelerate (e.g., decrease) the frame display rate. In one embodiment, for example, image comparison may be used. For example, if an image which is about to be displayed is substantially identical to an image currently displayed or recently displayed, then the frame display rate may be increased or gradually increased; whereas if an image which is about to be displayed is substantially different from an image currently displayed or recently displayed, then the frame display rate may be decreased, or may be reset to the "basic" frame display rate.

In another embodiment, an analysis of one or more image characteristics may be used to determine whether to accelerate, to maintain, or to decelerate the pace at which images are displayed. For example, brightness, darkness, illumination levels, image intensity, hue, saturation, contrast, color attributes, or other image characteristics may be compared or analyzed in order to determine whether neighboring (e.g., consecutive) in-vivo images are substantially similar or different.

In yet another embodiment, one or more image registration methods may be used to determine whether neighboring (e.g., consecutive) in-vivo images are substantially similar or different. This may include, for example, feature extraction, feature correspondence analysis, cross correlation, mutual information analysis, identification of overlapping image portions or features, or other methods for determining correspondence or similarity between multiple images.

In still another embodiment, other methods may be used to determine whether neighboring (e.g., consecutive) in-vivo images are substantially similar or different. For example, if a first image includes a close-up view of a body lumen wall, whereas a second image includes a tunnel-like view of an open body lumen, then it may be determined that the second image is substantially different from the first image, and the frame display rate, which may be an "accelerated" frame display rate at the first image, may be decreased or reset to the "basic" frame display rate at the second image. In some embodiments, one or more in-vivo image frames, or portions of the in-vivo image stream, may be classified based on the scenery or scenery-type included, and the acceleration or deceleration of the frame display rate may be performed by taking into account (or based on) such classification. Other suitable methods may be used.

In some embodiments, the modification of the frame display rate may be performed in real time or in display time, or substantially in real time or display time, and may depend on the frame in which the user (e.g., a physician) selects to begin viewing the image stream, or on the frame in which the user selects to continue to view the image stream.

In some embodiments, the acceleration of the frame display rate upon determination of a static portion of the image stream may be a gradual acceleration, such that the frame display rate increases gradually over multiple frames, e.g., as long as the image stream remains repetitive or non-changing, and until a pre-defined maximum acceleration rate is reached. For example, the frame display rate may gradually increase over several (e.g., consecutive or non-consecutive) in-vivo images, and/or during their display.

In some embodiments, workstation 117 may include, and/or monitor 118 may display, a user interface (UI), e.g., a graphical UI (GUI), which may allow the user, for example, to set or modify the "basic" frame display rate, to set or modify the "accelerated" frame display rate, to command the workstation 117 to display in-vivo images at a selected frame display rate (e.g., at the "basic" frame display rate, at the "accelerated" frame display rate, or the like), or the like. In some embodiments, for example, the GUI may allow the user to switch the workstation 117 among multiple frame display rates and/or among multiple modes of operation, e.g., a first mode of operation in which the in-vivo image stream is displayed using a constant frame display rate, a second mode of operation in which the in-vivo image stream is displayed using a variable frame display rate, a third mode of operation in which the in-vivo image stream is displayed using a mechanism that utilizes a "basic" and/or an "accelerated" frame display rate, or the like.

In some embodiments, monitor 118 may display an indication of the current frame display rate in use, an indication that the current frame display rate is "basic" or "accelerated", an indication of the relative acceleration of the frame display rate (e.g., twice the "basic" rate, three times the "basic" rate, or the like), an indication that a "static" or a "dynamic" portion of the in-vivo image stream is displayed or is about to be displayed, or the like. In some embodiments, monitor 118 may present a color indication or an alert, or workstation 117 may generate an audible alert, that the in-vivo image stream is displayed using an "accelerated" or non-"basic" frame display rate, for example, to alert the user of the current mode of operation.

In some embodiments, one or more of the indication described herein may be presented cumulatively, e.g., in one or more regions of the display of monitor 118. For example, in one embodiment, monitor 118 may present a first indication of the type of frame display rate (e.g., "basic" or "accelerated"), a second indication of the actual or absolute frame display rate being used (e.g., "2 FPS", "3 FPS", or the like), a third indication of the relative frame display rate (e.g., "×1 normal", "×2 acceleration", "×3 acceleration", or the like), a fourth indication of the scenery being displayed (e.g., "static", "dynamic", or the like), and/or other indications or GUI elements, e.g., timer, frame counter, time bar, progress bar, "slider" corresponding to the frame display rate, or the like. In one embodiment, two or more displayed items may share a common display region on monitor 118, for example, such that a first display item may replace a second display item, e.g., if the display items are alternative; for example, the indication "static" may replace the indication "dynamic", or the indication "basic rate" may replace the indication "accelerated rate", e.g., at the same area or display portion of the monitor 118; this may allow, for example, to save screen resources or display resources, and/or may allow over-crowding of the display with information.

Figure 2:
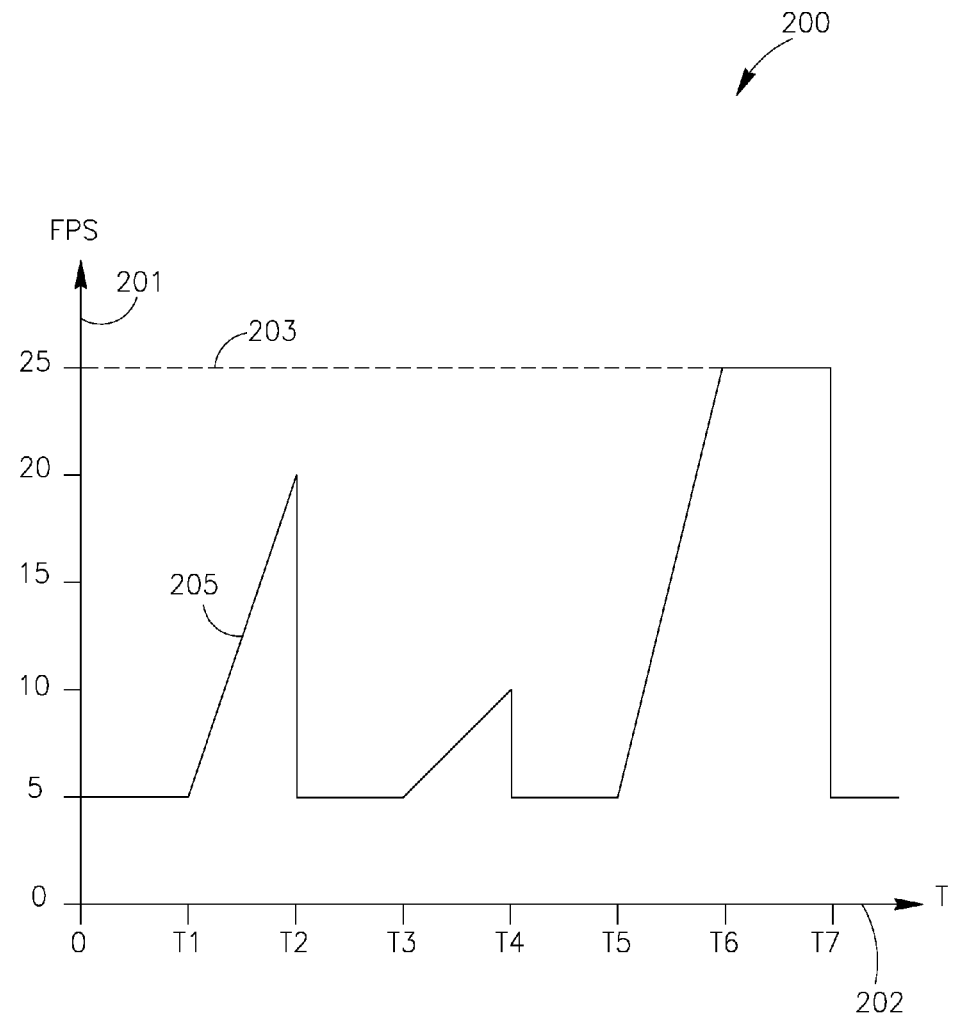
FIG. 2 is a schematic illustration of a demonstrative graph of frames per second (FPS) of displayed in-vivo images as a function of time (T) in accordance with an embodiment of the invention.

FIG. 2 schematically illustrates a demonstrative graph 200 of frames per second (FPS) of displayed in-vivo images as a function of time (T) in accordance with some embodiments of the invention. Graph 200 is presented for demonstrative purposes, and other types of graphs of patterns may be used in accordance with embodiments of the invention.

A vertical axis 201 may indicate, for example, a frame display rate of in-vivo images, for example, measured by FPS. A horizontal axis 202 may indicate, for example, elapsed time. Other suitable measurements or indication may be used; for example, the horizontal axis 202 may indicate or may correspond to, for example, progress of the in-vivo imaging device inside a body or a body lumen, a frame serial number of an in-vivo image serial number, or the like. Horizontal line 203 may indicate, for example, a maximum threshold value for the frame display rate, e.g., a maximum threshold value of 25 FPS. Other suitable values may be used. Graph line 205 may indicate the frame display rate utilized to display one or more in-vivo images as a function of time.

As shown in FIG. 2, for example, the portion of graph line 205 between time points T0 and T1 may be substantially horizontal, and may indicate that in the time period beginning at T0 and ending at T1, the frame display rate is substantially constant and may be equal to, for example, 5 FPS. For example, it may be determined (e.g., substantially in real time, while the in-vivo images stream is displayed, and not necessarily using pre-processing of the image stream) that the in-vivo images corresponding to the time period between T0 and T1 are substantially "dynamic" and/or varying, and therefore a "basic" or constant frame display rate of 5 FPS may be utilized during that time period.

The portion of graph 205 between time points T1 and T2 may gradually ascend or increase, for example, from the "basic" frame display rate of 5 FPS at time point T1, to an accelerated frame display rate of 20 FPS at time point T2. For example, it may be determined (e.g., substantially in real time, while the in-vivo images stream is displayed, and not necessarily using pre-processing of the image stream) that the in-vivo images corresponding to the time period between T1 and T2 are substantially "static" and/or repetitive and/or non-changing, and therefore an "accelerated" or a gradually increasing frame display rate of may be utilized during that time period.

As shown in FIG. 2, the frame display rate may decrease at time point T2, e.g., substantially abruptly or immediately, for example, from the "accelerated" frame display rate of 20 FPS, to the "basic" frame display rate of 5 FPS. This may be performed, for example, in response to a determination (e.g., substantially in real time, while the in-vivo images stream is displayed, and not necessarily using pre-processing of the image stream) that an in-vivo image about to be displayed (or being displayed) corresponding to time point T2 is different or substantially non-similar to the in-vivo image displayed immediately prior to time point T2. Therefore, the frame display rate may be reduced at time point T2, for example, the frame display rate may be reset to the "basic" frame display rate of 5 FPS.

The portion of graph line 205 between time points T2 and T3 may be substantially horizontal, and may indicate that in the time period beginning at T2 and ending at T3, the frame display rate is substantially constant and may be equal to, for example, 5 FPS. For example, it may be determined (e.g., substantially in real time, while the in-vivo images stream is displayed, and not necessarily using pre-processing of the image stream) that the in-vivo images corresponding to the time period between T2 and T3 are substantially "dynamic" and/or varying, and therefore a "basic" or constant frame display rate of 5 FPS may be utilized during that time period.

The portion of graph 205 between time points T3 and T4 may gradually ascend or increase, for example, from the "basic" frame display rate of 5 FPS at time point T3, to an accelerated frame display rate of 10 FPS at time point T4. For example, it may be determined (e.g., substantially in real time, while the in-vivo images stream is displayed, and not necessarily using pre-processing of the image stream) that the in-vivo images corresponding to the time period between T3 and T4 are substantially "static" and/or repetitive and/or non-changing, and therefore an "accelerated" or a gradually increasing frame display rate of may be utilized during that time period.

As shown in FIG. 2, the frame display rate may decrease at time point T4, e.g., substantially abruptly or immediately, for example, from the "accelerated" frame display rate of 10 FPS, to the "basic" frame display rate of 5 FPS. This may be performed, for example, in response to a determination (e.g., substantially in real time, while the in-vivo images stream is displayed, and not necessarily using pre-processing of the image stream) that an in-vivo image about to be displayed (or being displayed) corresponding to time point T4 is different or substantially non-similar to the in-vivo image displayed immediately prior to time point T4. Therefore, the frame display rate may be reduced at time point T4, for example, the frame display rate may be reset to the "basic" frame display rate of 5 FPS.

The portion of graph line 205 between time points T4 and T5 may be substantially horizontal, and may indicate that in the time period beginning at T4 and ending at T5, the frame display rate is substantially constant and may be equal to, for example, 5 FPS. For example, it may be determined (e.g., substantially in real time, while the in-vivo images stream is displayed, and not necessarily using pre-processing of the image stream) that the in-vivo images corresponding to the time period between T4 and T5 are substantially "dynamic" and/or varying, and therefore a "basic" or constant frame display rate of 5 FPS may be utilized during that time period.

The portion of graph 205 between time points T5 and T6 may gradually ascend or increase, for example, from the "basic" frame display rate of 5 FPS at time point T5, to an accelerated frame display rate of 25 FPS at time point T6. For example, it may be determined (e.g., substantially in real time, while the in-vivo images stream is displayed, and not necessarily using pre-processing of the image stream) that the in-vivo images corresponding to the time period between T5 and T6 are substantially "static" and/or repetitive and/or non-changing, and therefore an "accelerated" or a gradually increasing frame display rate of may be utilized during that time period.

The portion of graph line 205 between time points T6 and T7 may be substantially horizontal, and may indicate that in the time period beginning at T6 and ending at T7, the frame display rate is substantially constant and may be equal to the maximum frame display rate indicated by horizontal line 203, e.g., a value of 25 FPS. For example, it may be determined (e.g., substantially in real time, while the in-vivo images stream is displayed, and not necessarily using pre-processing of the image stream) that the in-vivo images corresponding to the time period between T6 and T7 are still "static" and/or repetitive and/or non-changing (e.g., similar to the in-vivo images corresponding to the time period between T5 and T6), but no further acceleration of the frame display rate may be performed, e.g., to avoid an increase of the frame display rate over the maximum frame display rate. Thus, the "accelerated" frame display rate may remain substantially constant and may equal to the value of the maximum frame display rate, e.g., 25 FPS, during the time period between T6 and T7.

As shown in FIG. 2, the frame display rate may decrease at time point T7, e.g., substantially abruptly or immediately, for example, from the "accelerated" frame display rate of 25 FPS, to the "basic" frame display rate of 5 FPS. This may be performed, for example, in response to a determination (e.g., substantially in real time, while the in-vivo images stream is displayed, and not necessarily using pre-processing of the image stream) that an in-vivo image about to be displayed (or being displayed) corresponding to time point T7 is different or substantially non-similar to the in-vivo image displayed immediately prior to time point T7. Therefore, the frame display rate may be reduced at time point T7, for example, the frame display rate may be reset to the "basic" frame display rate of 5 FPS.

Other suitable graphs or patterns may be used in conjunction with embodiments of the invention. Other suitable slopes or shapes may be used, for example, linear slopes, constantly or gradually increasing slopes, constantly or gradually decreasing slopes, exponentially increasing or decreasing slopes, or the like.

Figure 3:
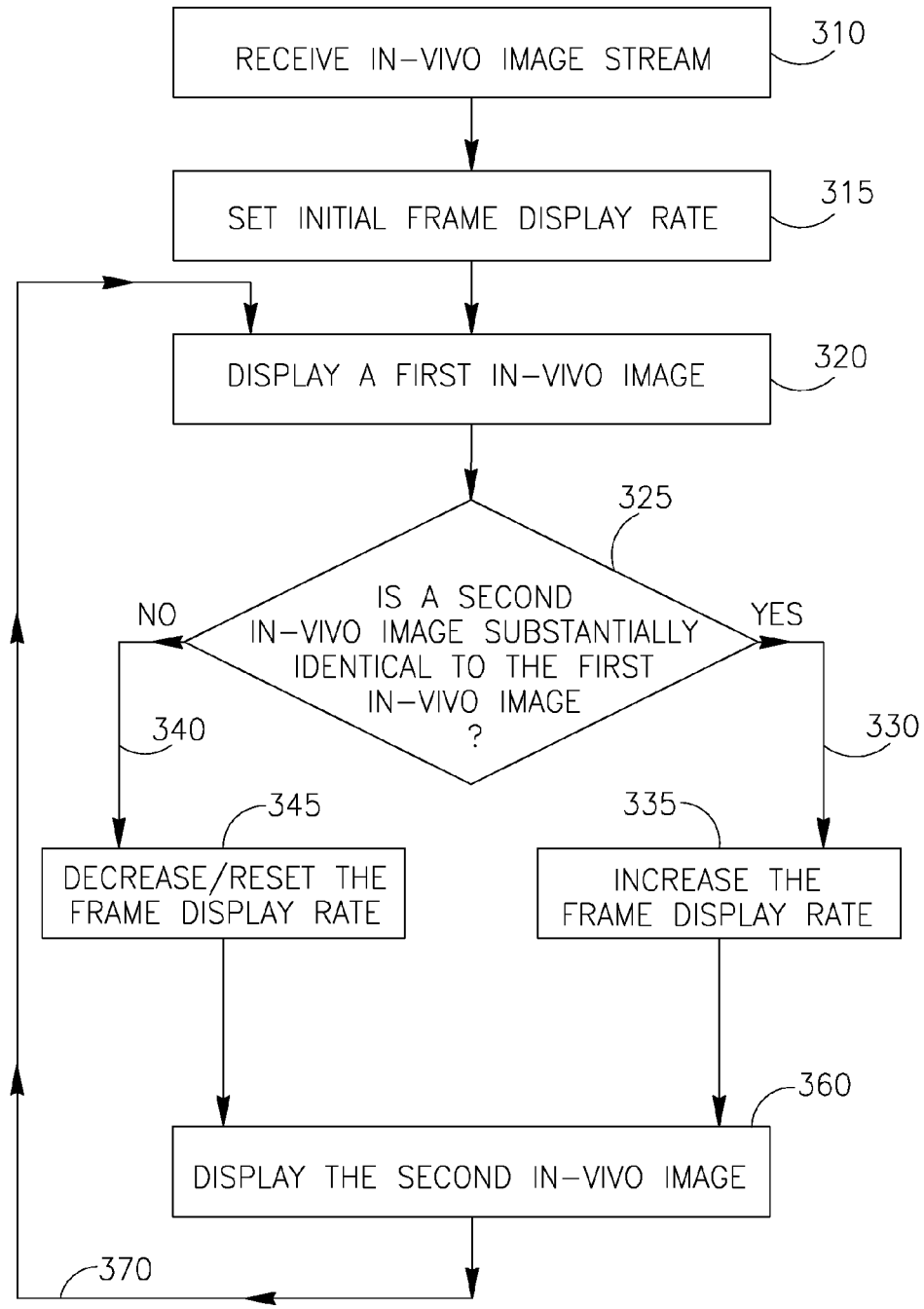
FIG. 3 is a flow-chart of a method of displaying in-vivo images at variable rate according to an embodiment of the invention.

FIG. 3 is a flow-chart of a method of displaying in-vivo images at variable rate in accordance with some embodiments of the invention. The method may be used, for example, in conjunction with one or more components, devices and/or systems described herein, and/or other suitable in-vivo devices and/or systems.

As indicated at box 310, the method may optionally include, for example, receiving an in-vivo image stream intended to be displayed. In some embodiments, for example, the in-vivo stream may be received by receiver/recorder 112 or workstation 117 of FIG. 1, e.g., from in-vivo imaging device 140 of FIG. 1. In some embodiments, the in-vivo image stream may include "raw" and/or non-processed in-vivo images, or "raw" and/or non-processed stream portions; for example, the received image stream may not be subject to pre-processing, e.g., a prior determination or classification of images or stream-portions as "static" or "dynamic", as changing or non-changing, as images or stream-portions associated with "basic" or "accelerated" frame display rate, or the like.

As indicated at box 315, the method may optionally include, for example, setting an initial frame display rate to a value of a "basic" (e.g., constant and/or non-accelerated) frame display rate. This may be performed, for example, upon beginning of a presentation of the in-vivo image stream in its beginning, and/or when a user instructs to begin or resume presentation at a certain time point or location. For example, in response to a user's request to "jump" to (e.g., directly access) a certain time point, e.g., a request to start or resume presentation at a certain time point, the frame display rate may be substantially immediately decreased and/or reset to the "basic" frame display rate.

As indicated at box 320, the method may optionally include, displaying an in-vivo image ("the first image" or the current image) at the "basic" frame display rate. This may include, for example, beginning to display an in-vivo image stream using the "basic" frame display rate. In some embodiments, this may be performed, for example, in response to a user's command to "play" or present the in-vivo image stream, or in response to a user's command to begin or resume presentation of the in-vivo image stream.

As indicated at box 325, the method may optionally include, for example, checking whether a subsequent in-vivo image ("the second image" or the next image), which is about to be displayed, is substantially identical or significantly similar to the first (e.g., currently-displayed or previously-displayed) image. The determination may be based on, or may include, one or more other operations, for example, comparison among in-vivo images, calculation of a difference score or a similarity score among in-vivo images, obtaining a pre-calculated difference score or similarity score, or the like.

As indicate by arrow 330, if the checking result is positive (e.g., if it is determined that the second image is substantially identical or significantly similar to the first image), then, as indicated at box 335, the method may optionally include, for example, increasing (e.g., gradually) the frame display rate. In some embodiment, the frame display rate may be increased only if the frame display rate is smaller than a pre-defined maximum threshold value of frame display rate. For example, if the current frame display rate being used is smaller than a pre-defined maximum threshold value of frame display rate, then the current frame display rate may be increased; whereas if the current frame display rate being used is not smaller than the pre-defined maximum threshold value of frame display rate, then the current frame display rate may be maintained and may not be increased.

In contrast, as indicated by arrow 340, if the checking result is negative (e.g., if it is determined that the second image is substantially different from the first image), then, as indicated at box 345, the method may optionally include, for example, decreasing or resetting the frame display rate to the "basic" or non-accelerated frame display rate.

As indicated at box 360, the method may optionally include, for example, displaying the second image utilizing the frame display rate determined in the operations of boxes 320, 335 and/or 345.

As indicated by arrow 370, the method may optionally include, for example, repeating one or more of the above operations. For example, upon displaying the second in-vivo image at box 360, the second image may be regarded as a new "first" image, which may be compared or otherwise analyzed in relation to a subsequent in-vivo image which is about to be displayed.

Other suitable operations or sets of operations may be used in accordance with embodiments of the invention.

In some embodiments, the in-vivo image stream may optionally include, for example, a group or a set of in-vivo image frames which are consolidated or otherwise combined into one image frame, e.g., using registration or other suitable methods. For example, the in-vivo image stream presented may not necessarily be a "raw" or un-processed image stream; the in-vivo image stream may be a processed image stream, or may include one or more processed portions or sections. In some embodiments, for example, multiple or alternative operations may be used to handle a set of in-vivo images. For example, in one embodiment, if two (or more) in-vivo images are substantially identical or are significantly similar, they may be consolidated or otherwise combined into (or replaced with) a single image frame; if two (or more) in-vivo images are similar (e.g., not significantly similar and not significantly different), they may be presented using a relatively high or accelerated frame display rate; and if two (or more) in-vivo images are different or non-similar, they may be presented using a relatively low or a "basic" frame display rate. Some embodiments of the present invention may be used, for example, in conjunction with one or more embodiments described in U.S. patent application Ser. No. 11/430,185, entitled "System and Method for Displaying an In-Vivo Image Stream", filed on May 9, 2006, which is hereby incorporated by reference in its entirety.

In some embodiments, an in-vivo image stream or a portion thereof may be presented in a forward direction (e.g., such that the displayed time advances from frame to frame), or in a backward or reverse direction (e.g., such that the displayed time is shown in a reverse order relative to the original in-vivo image stream). Accelerated, decelerated, increased and/or decreased frame display rate may be combined with forward and/or backward presentation of the in-vivo image stream or portion(s) thereof.

In some embodiments, multiple (e.g., two, four, or other number of) in-vivo image frames may be displayed simultaneously or substantially simultaneously. In some embodiments, the multiple in-vivo image frames may be combined, for example, using registration or other suitable methods. In one embodiment, for example, a combined image frame (or a simultaneous display of multiple in-vivo image frames) may be associated with a relatively low frame display rate, or may be presented for a relatively longer period of time.

In some embodiments, the system of FIG. 1 may acquire, process and/or present multiple in-vivo image streams, for example, substantially simultaneously. For example, device 140 may include multiple in-vivo imagers 146, e.g., two in-vivo imagers 146 facing substantially opposite directions, and may be able to simultaneously acquire and transmit two in-vivo image streams. In some embodiments, accelerated, decelerated, increased and/or decreased frame display rate may be used in conjunction with at least one of the two (or more) in-vivo image streams, or in conjunction with both (or all) the in-vivo image streams. In some embodiments, a first in-vivo image stream may be associated with a first frame display rate, e.g., an accelerated frame display rate; whereas a second (e.g., simultaneous) in-vivo image stream may be associated with a second frame display rate, e.g., "basic" or non-accelerated. In one embodiment, for example, workstation 117 may utilize the lower frame display rate to display multiple in-vivo image streams associated with different frame display rates.

In some embodiments, computation of differences among two (or more) in-vivo image frames may be performed in a pre-processing stage, and/or may be performed substantially in real time (e.g., during the presentation of the in-vivo stream); whereas the computation of the frame display rate may be performed while the in-vivo image stream is displayed, e.g., to take into account the "basic" frame display rate used when the presentation of the stream begins or resumes.

In some embodiments, optionally, a short pause may be introduced in the presentation of the in-vivo image stream upon switching from an "accelerated" frame display rate to the "basic" frame display rate. This may aid the user, for example, to further notice the change in frame display rate, or to otherwise adjust to the "basic" frame display rate.

In some embodiments, one or more algorithms (e.g., "look ahead" or "read ahead" algorithms) may be used to determine or modify the frame display rate. For example, the frame display rate may be decreased in advance, e.g., several frames prior to the time in which the "dynamic" or varying frame is actually sent for display. For example, in some embodiments, a frame display rate currently being used may be calculated based on similarity or difference across multiple in-vivo frames that are intended for display within one or two seconds. Other suitable anticipation algorithms may be used.

Various aspects of the various embodiments disclosed herein are combinable with the other embodiments disclosed herein.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A system for viewing an in-vivo image stream of a body lumen, the system comprising:
   an in-vivo device comprising an imager, an illumination source and a transmitter to transmit a stream of in vivo images captured by the imager, wherein the stream of in-vivo images comprises static image stream portions in which the images of the in-vivo image stream remain substantially non-changing and dynamic image stream portions in which the images of the in-vivo image stream change, wherein each of said static and dynamic image stream portions comprises multiple in-vivo image frames;
   a receiver configured to receive the transmitted stream of in vivo images; and
   a monitor configured to display the static image stream portions and the dynamic image stream portions, and to display, prior to display of a dynamic image stream portion or a static image stream portion, an indication alerting a user that a transition between a static image stream portion and said dynamic image stream portion and/or a transition between a dynamic image stream portion and said static image stream portion is about to occur.

2. The system of claim 1 wherein the monitor is further configured to display an indication that a static image stream portion or a dynamic image stream portion is being displayed.

3. The system of claim 1 further comprising a processor configured to increase a frame display rate of said static image stream portions to an accelerated frame display rate based on a similarity among multiple in-vivo images of said static image stream portions.

4. The system of claim 3, wherein the processor is further configured to increase a frame display rate of the in-vivo image stream over multiple in vivo image frames, from an initial frame display rate to a maximum frame display rate.

5. The system of claim 1, further comprising a processor configured to, upon detection of a difference between two or more in-vivo frames of said in-vivo image stream, decrease a frame display rate of said in-vivo image stream.

6. The system of claim 5 wherein decreasing the frame display rate occurs by immediately resetting the frame display rate to a normal or slower frame display rate relative to the increased frame display rate.

7. The system of claim 6 wherein the frame display rate is immediately reset to the initial frame display rate.

8. The system of claim 3, wherein the processor is further configured to reset the frame display rate from an accelerated frame display rate to a non-accelerated frame display rate in response to a command to begin displaying the in-vivo image stream from a selected point.

9. The system of claim 4 comprising a user interface which allows a user to set the value of the initial frame display rate.

10. The system of claim 9 wherein the processor is further configured to dynamically calculate the maximum frame display rate based on the value of the initial frame display rate.

11. The system of claim 3 wherein the monitor is further configured to display an indication of the current frame display rate being used, and an indication of the relative acceleration of the current frame display rate compared to the initial frame display rate.

12. The system of claim 3, wherein the processor is further configured to detect the similarity based on a comparative analysis of two or more of the multiple in-vivo images.

13. The system of claim 1 further comprising a processor configured to introduce a short pause in the display of the in-vivo image stream upon the transition between the static image stream portion and the dynamic image stream portion.

14. A method for displaying an in-vivo image stream of a body lumen, the method comprising:
receiving the in-vivo image stream of the body lumen from an in-vivo device comprising an imager, an illumination source and a transmitter configured to transmit the stream of in vivo images captured by the imager, wherein the stream of in-vivo images comprises static image stream portions in which the images of the in-vivo image stream remain substantially non-changing and dynamic image stream portions in which the images of the in-vivo image stream change, wherein each of said static and dynamic image stream portions comprises multiple in-vivo image frames; and
displaying the static image stream portions and the dynamic image stream portions on a monitor, and
displaying, prior to display of a dynamic image stream portion or a static image stream portion, an indication alerting a user that a transition from a static image stream portion to the dynamic image stream portion and/or a transition from a dynamic image stream portion to the static image stream portion is about to occur.

15. The method of claim 14 further comprising displaying an indication that the static image stream portion or the dynamic image stream portion is being displayed.

16. The method of claim 14 further comprising introducing a short pause in a display of the in-vivo image stream upon the transition between the static image stream portion and the dynamic image stream portion.

17. The method of claim 14, further comprising increasing a frame display rate of said static image stream portions to an accelerated frame display rate based on a similarity among multiple in-vivo images of said static image stream portions.

18. The method of claim 14, wherein upon detection of a difference between two or more in-vivo frames of said in-vivo image stream, the method further comprises decreasing the frame display rate of said in-vivo image stream.

19. The method of claim 17, further comprising resetting the frame display rate from an accelerated frame display rate to a non-accelerated frame display rate in response to a command to begin displaying the in-vivo image stream from a selected point.

20. The method of claim 17, further comprising displaying an indication of at least one of the current frame display rate being used and the relative acceleration of the current frame display rate compared to the initial frame display rate.

* * * * *